United States Patent
Yoshida et al.

[11] Patent Number: 6,127,564
[45] Date of Patent: Oct. 3, 2000

[54] SEMICARBAZINE/MANGANESE COMPLEX AND GAS GENERATOR FOR AIR BAG

[75] Inventors: Tadao Yoshida, Koshigaya; Shiro Chijiwa, Osaka; Yasuo Shimizu, Tokushima; Kazuo Hara, Tokushima; Takashi Kazumi, Shirakawa; Keisuke Matsuda; Kenichi Fukase, both of Fukushima, all of Japan

[73] Assignees: Otsuka Kagaku Kabushiki Kaisha, Osaka; Nippon Koki Co., Ltd., Tokyo, both of Japan

[21] Appl. No.: 09/331,774

[22] PCT Filed: Dec. 22, 1997

[86] PCT No.: PCT/JP97/04733

§ 371 Date: Jun. 24, 1999

§ 102(e) Date: Jun. 24, 1999

[87] PCT Pub. No.: WO98/29425

PCT Pub. Date: Jul. 9, 1998

[30] Foreign Application Priority Data

Dec. 26, 1996 [JP] Japan .................. 8-347715
May 23, 1997 [JP] Japan .................. 9-133354

[51] Int. Cl.[7] .............. C07F 13/00; C05D 5/06; B60R 21/26

[52] U.S. Cl. .............. 556/45; 252/1; 252/183.11; 280/728.1

[58] Field of Search ............... 556/45; 252/1, 252/183.11; 280/728.1

[56] References Cited

FOREIGN PATENT DOCUMENTS 9-104687  4/1997  Japan .
96/20147 A1  4/1996  WIPO .

*Primary Examiner*—Porfirio Nazario-Gonzalez
*Attorney, Agent, or Firm*—Armstrong, Westerman, Hattori, McLeland & Naughton

[57] ABSTRACT

The manganese complex of the invention is one represented by the formula (1)

$$[Mn(H_2NNHCONH_2)_3](NO_3)_2 \quad (1)$$

and showing weight loss of not higher than 1% after heating at 107° C. for 400 hours. The manganese complex has high heat stability and is used as an active component of an air bag gas generating composition. The air bag gas generating composition of the invention contains the above-mentioned manganese complex. The air bag gas generating composition comprising a complex mixture of the manganese complex and magnesium complex of semicarbazide and/or carbohydrazide features a high rate of combustion residue in an inflator.

18 Claims, No Drawings

SEMICARBAZINE/MANGANESE COMPLEX AND GAS GENERATOR FOR AIR BAG

TECHNICAL FIELD OF THE INVENTION

The present invention relates to a novel semicarbazide manganese complex and an air bag gas generating composition.

BACKGROUND ART

The air bag gas generating composition is required to have properties including (1) a suitable burning rate, (2) a low burning temperature, (3) capability of generating a large amount of gas, (4) low concentrations of toxic components in the generated gas and (5) a low shock ignitability. Further, there may arise a need for meeting stringent requirements that the air bag gas generating composition should retain the above-mentioned properties for a long term of at least 10 to 15 years even when, for example, a high temperature is maintained in an automobile in summer or at the tropics, desert area or the like for a long time or repeatedly. Whether an air bag gas generating composition can retain the required functions and can be stably used under such rigorous conditions for at least 10 to 15 years can be determined depending on whether the air bag gas generating composition can maintain the required properties after an accelerated heating test in which, for example, the composition is heated at 107° C. for 400 hours.

The inventors of the present invention previously discovered that a metal complex of semicarbazide is superior in the performance characteristics of air bag gas generating agents. The inventors completed an invention based on this discovery and filed a patent application in Japan under No.347715/1996. They made further investigations, directing their attention to a manganese complex of semicarbazide among metal complexes of semicarbazide, and found the following in the course of investigations. When a manganese complex of semicarbazide, like other metal complexes, is prepared by bringing semicarbazide into contact with manganese nitrate in an air atmosphere, the obtained manganese complex of semicarbazide, unlike other metal complexes, is not heat-stable. After an accelerated heating test of heating at 107° C. for 400 hours, the above complex shows weight loss of about 1.5 to about 5.2% or more and fails to maintain the required properties of air bag gas generating agents such as a suitable burning rate and low concentrations of toxic components in the generated gas.

Furthermore, an air bag gas generating composition is required to have a high rate of a combustion residue in an inflator.

A combustion residue is inevitably created by combustion of an air bag gas generating composition. Such combustion residue is separated by a filter disposed in an inflator from a gas generated by combustion of a gas generating composition. The inflator is designed to keep the combustion residue from leaking out of the inflator. If the combustion residue leaks out of the inflator, the air bag may be damaged, resulting in a likelihood of inflicting harm on the air bag user.

In recent years, there is a demand from automobile manufacturers for dimensional reduction of inflators compared with those heretofore used. To meet this demand, there is now a need for air bag gas generating compositions which have a property of showing a high rate of combustion residue in an inflator as the required properties of air bag gas generating compositions.

However, among the azide-based gas generating compositions and azide-free gas generating compositions heretofore proposed, those having this ability have not been developed.

For example, azide-based gas generating compositions, when burnt, give highly toxic sodium oxide ($Na_2O$) as a combustion residue. Therefore in this case, a filter should have a complicated structure for preventing the remainder from leaking out of the inflator. For this purpose, large-sized inflators are unavoidably used. Even if an inflator is designed to have a minimum size, currently its diameter is 100 mm at its smallest and can not be smaller than 100 mm.

On the other hand, azide-free gas generating compositions, for example, the metal complex of hydrazine and the metal complex of carbohydrazide disclosed in WO96/20147, are unsatisfactory in the rate of combustion residue in an inflator, failing to meet the above-mentioned need. In other words, when the metal complex of hydrazine and the metal complex of carbohydrazide disclosed in WO96/20147 are used, a structurally simplified filter can not be used for their low rate of combustion residue in an inflator, inevitably necessitating the use of a large-sized inflator. Currently the minimized diameter of a designed inflator is not smaller than 90 to 95 mm.

If we can develop an air bag gas generating composition assuring a high rate of combustion residue in an inflator, inflators could be made dimensionally smaller than those conventionally used. For example, inflators may be reduced in diameter to about 70 mm or less.

DISCLOSURE OF THE INVENTION

The present inventors conducted further research on the manganese complex of semicarbazide and found out a novel manganese complex of semicarbazide which has the above-mentioned required properties (1) to (5) of gas generating compositions, the complex being so heat-stable as to withstand said accelerated heating test.

Surprisingly the manganese complex of semicarbazide according to the invention assures weight loss of only 1% or less under the severe conditions of heating at 107° C. for 400 hours and is pronouncedly improved in heat stability. The highly heat-stable manganese complex of semicarbazide according to the invention is a novel compound undisclosed in literature.

The manganese complex of semicarbazide according to the invention assures weight loss of only 1% or less when heat-treated at 107° C. for 400 hours, namely is highly heat-stable. Consequently the complex can maintain the required properties (1) to (5) of air bag gas generating compositions for a long term of at least 10 to 15 years even under the rigorous conditions that a high temperature is maintained in an automobile for a long term or repeatedly.

The present inventors continued the research to develop an air bag gas generating composition which features a high rate of combustion residue in an inflator as well. As a result, the inventors found that a complex mixture of said heat-stable manganese complex of semicarbazide and a magnesium complex of semicarbazide and/or carbohydrazide in a specific mixing ratio is highly heat-stable and assures as well a high rate of combustion residue in an inflator.

For its high heat stability, the complex mixture of manganese complex and magnesium complex can maintain the required properties (1) to (5) of air bag gas generating compositions for a long term of at least 10 to 15 years even under the rigorous conditions that a high temperature is maintained in an automobile for a long time or repeatedly. Furthermore, the complex mixture can satisfactorily contribute to the reduction of inflator size because of its high rate of combustion residue in an inflator.

An object of the present invention is to provide a novel manganese complex of semicarbazide.

Another object of the invention is to provide a manganese complex of semicarbazide which is highly heat-stable and useful as a gas generating base for an air bag gas generating composition.

A further object of the invention is to provide a manganese complex of semicarbazide which is usable as an active component of an air bag gas generating composition capable of maintaining its functions for a long term of 10 to 15 years or longer even under rigorous conditions.

A still further object of the invention is to provide an air bag gas generating composition which contains the foregoing manganese complex of semicarbazide.

An additional object of the invention is to provide an air bag gas generating composition which assures a high rate of combustion residue in an inflator.

Another object of the invention is to provide an air bag gas generating composition which is highly heat-stable and capable of withstanding the use for a long term of 10 to 15 years or longer even under rigorous conditions, the composition assuring a high rate of combustion residue in an inflator.

Another object of the invention is to provide an air bag gas generating composition which enables the dimensional reduction of inflators.

According to the present invention, there is provided a manganese complex represented by the formula (1)

$$[Mn(H_2NNHCONH_2)_3](NO_3)_2 \qquad (1)$$

and showing weight loss of not higher than 1% after heating at 107° C. for 400 hours.

According to the present invention, there is also provided an air bag gas generating composition which comprises the manganese complex represented by the formula (1) and showing weight loss of not higher than 1% after heating at 107° C. for 400 hours (hereinafter referred to as "air bag gas generating composition A").

According to the present invention, there is also provided an air bag gas generating composition which comprises a complex mixture of (a) the manganese complex represented by the formula (1) and showing weight loss of not higher than 1% after heating at 107° C. for 400 hours and (b) a magnesium complex represented by the formula (2)

$$[Mg(X)_3](NO_3)_2 \qquad (2)$$

wherein X is $H_2NNHCONH_2$ or $H_2NNHCONHNH_2$, the mixing ratio, in terms of a weight ratio, of the component (a): the component (b) being 5:57-57:5 (hereinafter referred to as "air bag gas generating composition B").

Other features of the present invention are apparent from the following description.

The manganese complex of the invention is one represented by the formula (1)

$$[Mn(H_2NNHCONH_2)_3](NO_3)_2 \qquad (1)$$

and showing weight loss of not higher than 1% after heating at 107° C. for 400 hours.

The manganese complex of the invention assures weight loss of not higher than 1%, preferably not higher than 0.5%, namely pronouncedly small weight loss, after heating at 107° C. for 400 hours.

The manganese complex of the invention can be prepared by reacting manganese nitrate with semicarbazide in an atmosphere of inert gas.

In the practice of the invention, the reaction is conducted essentially in an atmosphere of inert gas to produce the highly heat-stable manganese complex of semicarbazide of the invention. When the reaction is carried out in an air atmosphere as disclosed in WO96/20147, only a manganese complex of semicarbazide of low heat stability is produced. At present, it remains to be clarified why the highly heat-stable manganese complex of semicarbazide can be prepared by the reaction in an atmosphere of inert gas.

Inert gases useful in the invention are not limited and include a wide range of conventional inert gases. Examples of such inert gases are nitrogen gas, helium gas, neon gas, argon gas and like rare gases. These inert gases can be used either alone or in combination. It is preferred in the invention to use nitrogen gas or argon gas from the viewpoints of operational efficiency and economy.

The reaction between manganese nitrate and semicarbazide may be carried out in the same manner as conventional methods except that the reaction is conducted in an atmosphere of inert gas.

For example, the reaction between manganese nitrate and semicarbazide can be carried out in a suitable solvent. Useful solvents include a wide range of conventional solvents which can dissolve manganese nitrate and semicarbazide. Examples are water, methanol, ethanol, propanol and like lower alcohols, and mixtures thereof.

The proportions of manganese nitrate and semicarbazide to be used are not limited and can be selected from a wide range. Usually about 1 to about 6 moles, preferably about 2 to about 4 moles, of semicarbazide is used per mole of manganese nitrate.

The reaction of manganese nitrate with semicarbazide is feasible either at room temperature or with cooling or heating and may be conducted at a temperature of 0 to about 100° C., preferably about 10 to about 50° C. The reaction time is variable depending on the reaction temperature and the like and is not specified. It is usually 4 hours or less, preferably 1 hour or less.

In the reaction of manganese nitrate with semicarbazide, it is desirable to mix a solution of manganese nitrate in a suitable solvent and a solution of semicarbazide in a suitable solvent.

A solution of manganese nitrate in a suitable solvent is mixed with a solution of semicarbazide in a suitable solvent essentially in an atmosphere of inert gas.

A solution of manganese nitrate in a suitable solvent and a solution of semicarbazide in a suitable solvent are preferably prepared in an atmosphere of inert gas.

After the completion of the reaction, a poor solvent is added to the reaction mixture and/or the reaction mixture is cooled, whereby the desired manganese complex is precipitated. Then, fractionation is conducted to obtain the manganese complex of the invention. The poor solvent may be mixed with water or a lower alcohol to be used as a solvent in the reaction for preparing a manganese complex, and is not limited insofar as the obtained complex has a lower dissolving power than water or a lower alcohol. Examples of such poor solvent include lower alcohols, acetonitrile, dioxane and the like when water is used as a solvent in the reaction and include acetonitrile, dioxane and the like when a lower alcohol is used as a solvent in the reaction.

The obtained manganese complex is isolated or purified by conventional separation or purification methods such as filtration, washing with an organic solvent (such as acetonitrile, alcohol, dioxane and like ethers), drying and the like.

The manganese complex obtained by the foregoing method brings about a weight decrease at a rate of not higher than 1% after heating at 107° C. for 400 hours, namely is highly heat-stable.

According to the invention, there is also provided an air bag gas generating composition.

The air bag gas generating composition A according to the invention comprises the manganese complex of the formula (1).

According to the invention, an air bag gas generating composition comprising an oxidizing agent as well as the manganese complex of the formula (1) is included in the air bag gas generating composition A.

The oxidizing agent to be used herein can be any of oxidizers commonly used in the art and includes, for example, salts of nitric acid, salts of oxohalogen acids, peroxides, etc. Among them, salts of nitric acid are preferred.

Examples of salts of nitric acid include a wide range of those known, and are alkali metal salts such as lithium nitrate, sodium nitrate and potassium nitrate, alkaline earth metal salts such as barium nitrate and strontium nitrate, ammonium salts such as ammonium nitrate, and so on. Among them, alkali metal salts and alkaline earth metal salts are preferred, and potassium nitrate and strontium nitrate are especially preferred.

Usable oxohalogen acid salts include a wide variety of those known, for example, perhalogenates, halogenates and the like. Examples of perhalogenates are alkali metal salts such as lithium perchlorate, potassium perchlorate, sodium perchlorate, lithium perbromate, potassium perbromate and sodium perbromate, alkaline earth metal salts such as barium perchlorate, calcium perchlorate, barium perbromate and calcium perbromate, ammonium salts such as ammonium perchlorate and ammonium perbromate, etc. Examples of useful halogenates are alkali metal salts such as lithium chlorate, potassium chlorate, sodium chlorate, lithium bromate, potassium bromate and sodium bromate, alkaline earth metal salts such as barium chlorate, calcium chlorate and calcium bromate, ammonium salts such as ammonium chlorate and ammonium bromate, etc. Among them, alkali metal perhalogenates and alkali metal halogenates are preferred.

Examples of the peroxide include a wide variety of those known, for example, peroxides of alkali metals such as lithium peroxide, potassium peroxide and sodium peroxide, peroxides of alkaline earth metals such as calcium peroxide, strontium peroxide and barium peroxide.

These oxidizing agents can be used either alone or in combination. Commercially available products of these oxidizing agents can be used as such, and the shape, particle size and the like are not limited and can be properly selected from a wide range in accordance with, for example, the amount of the oxidizing agent, the proportions to other components, the volume of the air bag and other conditions.

The oxidizing agent is used usually in a stoichiometric amount sufficient to completely oxidize and burn the manganese complex, calculated on the basis of the amount of oxygen. The amount of the oxidizing agent can be properly selected from a wide range, since the burning rate, burning temperature (gas temperature), composition of the combustion gas, etc. can be adjusted as desired by suitably changing the amounts of the manganese complex and the oxidizing agent. The oxidizing agent is used in an amount of about 10 to about 400 parts by weight, preferably about 20 to about 200 parts by weight, more preferably about 30 to about 100 parts by weight, per 100 parts by weight of the manganese complex.

The air bag gas generating composition B according to the invention comprises (a) the manganese complex represented by the formula (1) and (b) the magnesium complex represented by the formula (2) in a mixing ratio, in terms of a weight ratio, of the former to the latter of 5:57-57:5.

According to the invention, an air bag gas generating composition comprising an oxidizing agent as well as the manganese complex of the formula (1) and the magnesium complex of the formula (2) is included in the air bag gas generating composition B.

The magnesium complex used as the component (b) in the invention is one represented by the formula (2)

$$[Mg(X)_3](NO_3)_2 \qquad (2)$$

wherein X is as defined above.

The magnesium complexes to be used in the invention include a semicarbazide magnesium complex represented by the formula (3)

$$[Mg(H_2NNHCONH_2)_3](NO_3)_2 \qquad (3)$$

and a carbohydrazide magnesium complex represented by the formula (4)

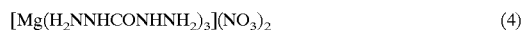

$$[Mg(H_2NNHCONHNH_2)_3](NO_3)_2 \qquad (4)$$

The magnesium complex of the formula (2) to be used in the invention can be prepared as by reacting magnesium nitrate with semicarbazide or carbohydrazide. The reaction may be conducted in either an inert atmosphere or an air atmosphere. The magnesium complex of the formula (2), too is superior in heat stability.

In the practice of the invention, the semicarbazide magnesium complex of the formula (3) and the carbohydrazide magnesium complex of the formula (4) may be used as the component (b) individually or as a mixture.

It is essential in the invention to use, as the active component of the air bag gas generating composition B, the complex mixture of the manganese complex as the component (a) and the magnesium complex as the component (b) in a mixing ratio, in terms of a weight ratio, of the component (a) to the component (b) of 5:57-57:5.

When the mixing ratio of the components (a) and (b) is outside the foregoing range, i.e. in either case of the proportion of component (a) above or below the foregoing range, the resulting air bag gas generating composition is low in the rate of combustion residue in an inflator, in other words, the air bag gas generating composition as contemplated by the invention can not be obtained.

It is desirable in the invention to use, as the active component of the air bag gas generating composition B, the complex mixture of the manganese complex as the component (a) and the magnesium complex as the component (b) in a mixing ratio, in terms of a weight ratio, of the component (a) to the component (b) of 20:42–52:10.

It is especially desirable in the invention to use, as the active component of the air bag gas generating composition B, the complex mixture of the manganese complex as the component (a) and the magnesium complex as the component (b) in a mixing ratio, in terms of a weight ratio, of the component (a) to the component (b) of 35:27–45:17. When such complex mixture is used, the obtained air bag gas generating composition is highly heat-stable and results in a pronouncedly high rate of combustion residue in an inflator.

Given below are examples of the complex mixture of the components (a) and (b) (hereinafter referred to merely as "complex mixture"):

a complex mixture of, as the component (a), a semicarbazide manganese complex represented by the formula (1)

$$[Mn(H_2NNHCONH_2)_3](NO_3)_2 \qquad (1)$$

and showing weight loss of not higher than 1% after heating at 107° C. for 400 hours and, as the component (b), a semicarbazide magnesium complex represented by the formula (3)

$$[Mg(H_2NNHCONH_2)_3](NO_3)_2 \quad (3)$$

a complex mixture of, as the component (a), a semihydrazide manganese complex represented by the formula (1)

$$[Mn(H_2NNHCONH_2)_3](NO_3)_2 \quad (1)$$

and showing weight loss of not higher than 1% after heating at 107° C. for 400 hours and, as the component (b), a carbohydrazide magnesium complex represented by the formula (4)

$$[Mg(H_2NNHCONHNH_2)_3](NO_3)_2 \quad (4)$$

The oxidizing agent to be incorporated in the air bag gas generating composition B according to the invention may be of the same type as that in the air bag gas generating composition A and may be used in the same amount as in the composition A.

The air bag gas generating compositions A and B may contain at least one species selected from exhaust gas modifiers and binders in addition to the manganese complex or the complex mixture of manganese complex and magnesium complex and the oxidizing agent.

The exhaust gas modifier presumably has an activity chiefly to reduce the concentrations of toxic components such as CO, NOx and the like in the exhaust gas.

Usable exhaust gas modifiers include a wide range of those known in the art and are, for example, silicides of elements of the 4th to 6th periods in the periodic table.

Examples of silicides of elements of the 4th period are titanium silicide, chromium silicide and the like. Examples of silicides of elements of the 5th period are zirconium silicide, niobium silicide, molybdenum silicide and the like. Examples of silicides of elements of the 6th period are tantalum silicide, tungsten silicide and the like.

These exhaust gas modifiers can be used either alone or in combination. Commercially available products of these exhaust gas modifiers can be used as such. The particle size of the exhaust gas modifier is not limited and can be properly selected from a wide range in accordance with, for example, the amount of the exhaust gas modifier, the proportions to other components, the volume of the air bag and other conditions. The amount of the exhaust gas modifier to be used is not limited and can be properly selected from a wide range in accordance with, for example, the proportions to other components, the volume of the air bag and other conditions. The amount is about 0.1 to about 20 parts by weight, preferably about 1 to about 10 parts by weight, per 100 parts by weight of the total amount of the manganese complex or the complex mixture of manganese complex and magnesium complex and the oxidizing agent.

The binder is used chiefly for molding the gas generating composition into tablets or the like and has further activities to reduce the burning temperature and to adjust the burning rate.

Useful binders include a wide range of those known in the art such as cellulose compounds, thermoplastic resins, organic high molecular compounds, inorganic binders, etc.

Examples of the cellulose compound are carboxtnethyl cellulose, hydroxymethyl cellulose, ethers thereof, microcrystalline cellulose powders, etc. Among them, microcrystalline cellulose powders are preferable to use. For example, the powders available under a trade name "Abicel" manufactured by Asahi Chemical Co., Ltd.) can be used.

Examples of the thermoplastic resin are polypropylene carbonate, polyethylene/polyvinyl acetate copolymer, styrene/polyester copolymer, polyethyleneimide, polyvinyl ether, polyvinyl butyral, polyacrylamide, maleic acid polymer, hydroxy-terminated polybutadiene-based thermoplastic polyurethane, polybutadiene/acrylonitrile copolymer, carboxyl-terminated polybutadiene-based polyester, acrylate-terminated polybutadiene, ester of polybutadiene polycarboxylic acid with hydroxy-terminated poybutadiene, acrylic latex suspension, etc. Among them, preferred are polyethylene/polyvinyl acetate copolymer, polyvinyl ether, polyvinyl butyral and the like.

Useful organic high molecular compounds are, for example, soluble starch, polyvinyl alcohol, partially saponified products thereof, polyethylene glycol, polypropylene glycol, polyvinyl pyrrolidone, polysaccharide, sodium polyacrylate, ammonium polyacrylate, etc. Among them, soluble starch, polyvinyl alcohol and the like are preferred.

Useful inorganic binders are, for example, silica sol, alumina sol, zirconia sol, etc.

Among the above binders, cellulose compounds, thermoplastic resins and the like are preferred.

These binders can be used either alone or in combination. Commercially available products of these binders can be used as such. The particle size of the binder is not limited and can be properly selected from a wide range in accordance with, for example, the amount of the binder, the proportions to other components, the volume of the air bag and other conditions. The amount of the binder to be used is not limited and can be properly selected from a wide range in accordance with, for example, the proportions to other components, the volume of the air bag and other conditions. The amount is about 0.1 to about 20 parts by weight, preferably about 1 to about 10 parts by weight, per 100 parts by weight of the total amount of the manganese complex or the complex mixture of manganese complex and magnesium complex and the oxidizing agent.

The air bag gas generating compositions A and B according to the invention may contain additives conventionally used for gas generating compositions. Examples of useful additives are carbonates and silicates of alkali metals such as sodium carbonate, potassium carbonate, sodium silicate, potassium silicate and the like, oxides of elements of the 2nd and 3rd periods of the periodic table such as bentonite, alumina, diatomaceous earth, silicon dioxide, boron oxide and the like. These additives have activities to improve the properties of the gas generating composition of the invention and to facilitate molding the gas generating composition of the invention into tablets or the like. The amount of the additive to be used is not limited and can be properly selected from a wide range. The amount is about 0.01 to about 10 parts by weight, preferably about 0.05 to about 5 parts by weight, per 100 parts by weight of the total amount of the manganese complex or the complex mixture of manganese complex and magnesium complex and the oxidizing agent.

The air bag gas generating compositions A and B according to the invention may contain gas generating bases and other additives conventionally used insofar as they do not adversely affect the contemplated result of the invention.

The air bag gas generating compositions A and B according to the invention can be prepared by mixing the manganese complex or the complex mixture of manganese complex and magnesium complex, the oxidizing agent and other optional components.

For use, the air bag gas generating compositions A and B according to the invention is molded into a suitable shape.

For example, the manganese complex or the complex mixture of manganese complex and magnesium complex and oxidizing agent are mixed with the binder and other optional components. The mixture is granulated when so required, tabletted and optionally dried into a molded product. In granulation, a small amount of water, alcohol, ether or like organic solvent may be added to facilitate the operation or to assure increased safety in the operation. The molding operation is preferably carried out in an inert atmosphere.

The shape of the preparation is not limited and includes, for example, pellets, disks, balls, bars, hollow cylinders, confetti and tetrapods. It may be solid or porous (e.g. honeycomb-shaped). One or more projections may be formed on one or both of surfaces of pellets or disks. The shape of the projections is not limited and includes, for example, cylinders, cones, polygonal cones, polygonal pillars, etc.

According to the invention, the manganese complex and the air bag gas generating composition A can be concurrently prepared. For example, manganese nitrate, semicarbazide, oxidizing agent and other optional components are mixed together, followed by addition of a suitable amount of water, lower alcohol or the like. In this case, the mixture can be molded into a suitable shape in the same manner as above.

According to the invention, the manganese complex and magnesium complex, and the air bag gas generating composition B can be concurrently prepared. For example, the manganese nitrate, magnesium nitrate, semicarbazide and/or carbohydrazide, oxidizing agent and other optional components are mixed together in an inert atmosphere, followed by addition of a suitable amount of water, lower alcohol or the like. In this case, the mixture can be molded into a suitable shape in the same manner as above.

BEST MODE FOR CARRYING OUT THE INVENTION

Given below are Examples and Comparative Examples to clarify the present invention.

REFERENCE EXAMPLE 1 (Preparation of semicarbazide)

A 40.0 g (1.0 mole) quantity of sodium hydroxide was dissolved in 1000 ml of ethanol. Then, 111.5 g (1.0 mole) of semicarbazide hydrochloride was added with stirring at room temperature. The mixture was heated to 60° C. to undergo a reaction for 2 hours. After confirming that the reaction mixture became neutral, it was filtered while remaining hot. Then, the filtrate was cooled to not higher than 10° C. The precipitated solid was separated by filtration, washed with a small amount of ethanol and dried, giving 63.8 g of white solid of semicarbazide (yield 85%).

Elementary analysis (for $H_2NNHCONH_2$);

|  | C | H | N |
|---|---|---|---|
| Calcd. (%) | 15.99 | 6.71 | 55.95 |
| Found (%) | 15.68 | 6.50 | 56.00 |

IR (cm-1): 551, 772, 937, 983, 1102, 1175, 1364, 1469, 1668, 3340, 3447; Weight decrease-starting temperature (TG): 164° C.

EXAMPLE 1 (Preparation of semicarbazide manganese complex)

A 22.5 g (0.3 mole) quantity of semicarbazide was dissolved in 50 ml of water in a nitrogen atmosphere. Nitrogen was refluxed in a 500 ml 4-necked flask to replace the air in the flask with nitrogen. While in a nitrogen atmosphere, the flask was charged with 28.7 g (0.1 mole) of hexahydrated manganese (II) nitrate and 100 ml of water to dissolve the hexahydrated manganese (II) nitrate in water. The semicarbazide solution obtained above was added to the flask with stirring at room temperature. After stirring for a further 10 minutes, the reaction solution was placed into an eggplant type flask. After the air was replaced with nitrogen, the reaction solution was concentrated under reduced pressure. Nitrogen was introduced into the eggplant type flask containing the concentrated reaction solution. Thereafter the flask was dipped into an ice bath to cool the concentrated reaction solution. Then 50 ml of methanol was added to the reaction solution under a nitrogen atmosphere to give a suspension. After separation of the solid by filtration, the solid was washed with a small amount of methanol and vacuum-dried, giving a pale purple solid.

The reaction product was $[Mn(H_2NNHCONH_2)_3](NO_3)_2$. Amount yielded 32 g. Yield 79%.

Elementary analysis (for $[Mn(H_2NNHCONH_2)_3](NO_3)_2$)

|  | C | H | N |
|---|---|---|---|
| Calcd. (%) | 8.91 | 3.71 | 38.10 |
| Found (%) | 9.19 | 3.59 | 38.03 |

IR (cm$^{-1}$): 563, 715, 766, 833, 1086, 1121, 1198, 1385, 1547, 1590, 1655, 1634, 2428, 3174, 3250, 3445; Weight decrease-starting temperature (TG): 210° C.

EXAMPLE 2 (Preparation of semicarbazide manganese complex)

In this example, the procedure of Example 1 was repeated on a scale-up basis.

A 225 g (3 moles) quantity of semicarbazide was dissolved in 500 ml of water in a nitrogen atmosphere. Nitrogen was refluxed in a 5 liter 4-necked flask to replace the air in the flask with nitrogen. While in a nitrogen atmosphere, the flask was charged with 287 g (1 mole) of hexahydrated manganese (II) nitrate and 1 liter of water to dissolve the hexahydrated manganese (II) nitrate in water. The semicarbazide solution obtained above was added to the flask with stirring at room temperature. After stirring for a further 10 minutes, the reaction solution was placed into an eggplant type flask. After the air was replaced with nitrogen, the reaction solution was concentrated under reduced pressure. Nitrogen was introduced into the eggplant type flask containing the concentrated reaction solution. The flask was dipped into an ice bath to cool the concentrated reaction solution. Then, 500 ml of methanol was added to the reaction solution under a nitrogen atmosphere to give a suspension. After separation of the solid by filtration, the solid was washed with a small amount of methanol and vacuum-dried, giving a whitish or purplish solid.

The reaction product was $[Mn(H_2NNHCONH_2)_3](NO_3)_2$. Amount yielded 350 g. Yield 86%

The results of elementary analysis and IR spectrum were the same as those of the solid obtained in Example 1. Weight decrease-starting temperature (TG): 214° C.

COMPARATIVE EXAMPLE 1 (Preparation of semicarbazide manganese complex)

A 22.5 g (0.3 mole) quantity of semicarbazide was dissolved in 50 ml of water. A 28.7 g (0.1 mole) quantity of hexahydrated manganese (II) nitrate was dissolved in 100 ml of water. The semicarbazide solution obtained above was added with stirring at room temperature. After 10 minute-stirring, the reaction solution was concentrated. Thereafter the concentrated reaction solution was cooled in an ice bath. Then, 50 ml of methanol was added to the reaction solution to give a suspension. After separation of the solid by filtration, the solid was washed with a small amount of methanol and vacuum-dried, giving a pale purple solid.

The reaction product was $[Mn(H_2NNHCONH_2)_3](NO_3)_2$. Amount yielded 34 g. Yield 84%.

The results of elementary analysis and IR spectrum were the same as those of the solid obtained in Example 1. Weight decrease-starting temperature (TG): 210° C.

COMPARATIVE EXAMPLE 2 (Preparation of semicarbazide manganese complex)

In this comparative example, the procedure of Comparative Example 1 was carried out on a scale-up basis.

A 225 g (3 moles) quantity of semicarbazide was dissolved in 500 ml of water. A 287 g (1 mole) quantity of hexahydrated manganese (II) nitrate was dissolved in 1000 ml of water. The semicarbazide solution obtained above was added with stirring at room temperature. After 10 minute-stirring, the reaction solution was concentrated. The concentrated reaction solution was cooled in an ice bath. Then, 500 ml of methanol was added to the reaction solution to give a suspension. After separation of the solid by filtration, the solid was washed with a small amount of methanol and vacuum-dried, giving a whitish or purplish solid.

The reaction product was $[Mn(H_2NNHCONH_2)_3(NO_3)_2$. Amount yielded 300 g. Yield 74%.

The results of elementary analysis and IR spectrum were the same as those of the solid obtained in Example 1. Weight decrease-starting temperature (TG): 207° C. (a slight weight decrease started to occur at 170° C.)

TEST EXAMPLE 1

The semicarbazide manganese complexes prepared in Examples 1 and 2, and Comparative Examples 1 and 2 were checked for heat stability by the following method.

Ten grams of each semicarbazide manganese complex was placed into a weighing bottle made of glass. Then the glass bottle was introduced into a thermostatic container at 107° C. The weight loss of the complexes was determined after standing for 100 hours and 400 hours. The results are shown in Table 1.

TABLE 1

|  | Weight decrease rate after 100 hrs (%) | Weight decrease rate after 400 hrs (%) |
| --- | --- | --- |
| Example 1 | 0.05 | 0.21 |
| Example 2 | 0.08 | 0.19 |
| Comp. Ex. 1 | 0.41 | 1.54 |
| Comp. Ex. 2 | 0.69 | 5.24 |

Even after standing for 400 hours under the heating conditions of 107° C., the semicarbazide manganese complexes of the invention showed notably small weight loss. This denotes that these complexes had high heat stability. On the other hand, it is clear especially from the scale-up procedures that the semicarbazide manganese complexes prepared by the methods of Comparative Examples had low heat stability.

EXAMPLE 3

A gas generating composition was prepared using the semicarbazide manganese complex obtained in Example 2 after heat treatment at 107° C. for 400 hours. Namely, a moist powder was prepared by mixing together 63 parts by weight of the heat-treated manganese complex, 34 parts by weight of potassium nitrate and 3 parts by weight of microcrystalline particles (binder, trade name "Abicel", product of Asahi Kagaku Kogyo Co., Ltd.). The moist powder was granulated by a granulator. After drying, the granules were compressed using a cam-type tablet molding machine to give pellets of a gas generating composition (4 mm in diameter, 1.5 mm in height and 0.05 g in mass).

CONTROL EXAMPLE 1

Pellets of a gas generating composition were prepared in the same manner as in Example 3 with the exception of using 63 parts by weight of the semicarbazide manganese complex of Example 2 without heat treatment.

TEST EXAMPLE 2

Forty-five grams of each of the pellet samples of the gas generating compositions prepared in Example 3 and Control Example 1 was individually filled into the combustion chamber of an inflator having a gas outlet 4 mm in diameter and loaded with 3.0 g of boron/potassium nitrate as a transfer charge. An aluminum tape 0.15 mm in thickness was attached to the gas outlet to maintain the pressure. The inflator was set in a 60-liter tank and actuated by applying a current to ignition means to thereby ignite the pellet sample. Then, there were determined the maximum pressure in the combustion chamber (MPa), time in which the internal pressure of the combustion chamber reaches the maximum (ms), and time in which the internal pressure of the 60-liter tank reaches the maximum (ms) After burning, the gas in the 60-liter tank was collected into a 10-liter tedlar bag, and the CO and NOx concentrations were measured using a detector tube. The results are shown in Table 2.

TABLE 2

|  | Example 3 | Control Example 1 |
| --- | --- | --- |
| Maximum pressure in the combustion chamber (MPa) | 23.0 | 23.1 |
| Time in which the internal pressure of the combustion chamber reaches the maximum | 4.4 | 4.3 |
| Time in which the internal pressure of the 60-liter tank reaches the maximum | 59.9 | 59.9 |
| Quantity of generated gas (mole) | 3 | 3 |
| CO concentration (%) | 1.2 | 1.2 |
| NOx concentration (ppm) | 600 | 600 |

It was confirmed that excellent properties were shown by any of, as a gas generating agent, the semicarbazide manganese complex obtained in Example 2 (Control Example 1) and the semicarbazide manganese complex obtained in Example 2 and heat-treated at 107° C. for 400 hours (Example 3).

For example, the gas generating agents obtained in Example 3 and Control Example 1 reached the maximum internal pressure in less than 60 ms when tested in the 60-liter tank, which means that the agents had a burning rate sufficient to inflate the air bag.

The gas generating agents obtained in Example 3 and Control Example 1 generated a large amount of gas and contained toxic components in low concentrations. Conventional gas generating agents which contain, as a gas generating base, a nitrogen-containing organic compound having an amino group generate 2 to 2.5 moles of gas and have a CO content of about 2%.

The semicarbazide manganese complex obtained in Example 2 and heat-treated at 107° C. for 400 hours was used in Examples 4 to 9 and Comparative Examples 3 and 4 to be described below.

EXAMPLE 4

A moist powder was prepared by mixing 52 parts by weight of a semicarbazide manganese complex, 10 parts by weight of a semicarbazide magnesium complex, 35 parts by weight of strontium nitrate and 3 parts by weight of a microcrystalline cellulose powder (binder, a trade name "Abicel" manufactured by Asahi Kagaku Kogyo Co., Ltd.). The moist powder was granulated by a granulator. After drying, the granules were compressed using a cam-type tablet molding machine to give pellets of a gas generating composition (4 mm in diameter, 1.5 mm in height and 0.05 g in mass).

EXAMPLES 5 to 8

Pellets of gas generating compositions were prepared in the same manner as in Example 4 with the exception of changing the amounts of the semicarbazide manganese complex and semicarbazide magnesium complex as shown in Table 3.

COMPARATIVE EXAMPLE 3

A moist powder was prepared by mixing 62 parts by weight of a semicarbazide manganese complex, 35 parts by weight of strontium nitrate and 3 parts by weight of a microcrystalline cellulose powder (binder, a trade name "Abicel" manufactured by Asahi Kagaku Kogyo Co., Ltd.). Pellets of a gas generating composition were prepared by repeating the subsequent procedure of Example 4.

COMPARATIVE EXAMPLE 4

A moist powder was prepared by mixing 62 parts by weight of a semicarbazide magnesium complex, 35 parts by weight of strontium nitrate and 3 parts by weight of a microcrystalline cellulose powder (binder, a trade name "Abicel" manufactured by Asahi Kagaku Kogyo Co., Ltd.). Pellets of a gas generating composition were prepared by repeating the subsequent procedure of Example 4.

TEST EXAMPLE 3

Forty-five grams of each of the pellet samples of the gas generating compositions prepared in Examples 4 to 8 and Comparative Examples 3 and 4 was individually filled into the combustion chamber of an inflator having a gas outlet 4 mm in diameter and loaded with 3.0 g of boron/potassium nitrate as a transfer charge. An aluminum tape 0.15 mm in thickness was attached to the gas outlet to maintain the pressure. The inflator was set in a 60-liter tank and actuated by applying a current to ignition means to thereby ignite the pellet sample. Then, there were determined the maximum pressure in the combustion chamber (MPa) and time in which the internal pressure of the combustion chamber reaches the maximum (ms). After burning, the amount of the remainder in the combustion chamber of the inflator was measured. The results are shown in Table 3. In Table 3, MnSC is an abbreviation of the semicarbazide manganese complex and MgSC is an abbreviation of the semicarbazide magnesium complex.

TABLE 3

| | Comp. Ex. 3 | Ex. 4 | Ex. 5 | Ex. 6 | Ex. 7 | Ex. 8 | Comp. Ex. 4 |
|---|---|---|---|---|---|---|---|
| MnSC (wt. part) | 62 | 52 | 42 | 31 | 20 | 10 | 0 |
| MgSC (wt. part) | 0 | 10 | 20 | 31 | 42 | 52 | 62 |
| Strontium nitrate (wt. part) | 35 | 35 | 35 | 35 | 35 | 35 | 35 |
| Crystalline cellulose (wt. part) | 3 | 3 | 3 | 3 | 3 | 3 | 3 |
| Maximum pressure in combustion chamber (MPa) | 22.5 | 20.7 | 21.1 | 21.0 | 21.7 | 22.2 | 23.0 |
| Time for pressure to reach maximum in combustion chamber (ms) | 4.4 | 4.3 | 4.5 | 4.4 | 4.2 | 4.4 | 4.4 |
| Rate of combustion remainder (%) | 53.7 | 71.3 | 77.0 | 73.3 | 72.1 | 69.0 | 50.5 |

EXAMPLE 9

Pellets of a gas generating composition were prepared in the same manner as in Example 4, using 43 parts by weight of a semicarbazide manganese complex, 20 parts by weight of a semicarbazide magnesium complex, 34 parts by weight of potassium nitrate and 3 parts by weight of a microcrystalline cellulose powder (binder, a trade name "Abicel" manufactured by Asahi Kagaku Kogyo Co., Ltd.).

In the same manner as in Test Example 3, the pellets of the gas generating composition obtained in Example 9 were checked to determine the maximum pressure in the combustion chamber (MPa), time in which the internal pressure of the combustion chamber reaches the maximum (ms), and the amount of the remainder in the combustion chamber of the inflator after burning.

As a result, the maximum pressure in the combustion chamber was 21.7 (MPa), the time for the internal pressure of the combustion chamber to reach the maximum was 3.6 (ms), and the rate of the remainder in the combustion chamber of the inflator after burning was 75.3%.

TEST EXAMPLE 4

Forty-five grams of each of the pellet samples of the gas generating compositions prepared in Example 5 and Comparative Example 4 was individually filled into the combustion chamber of an inflator having a gas outlet 3 mm in diameter and loaded with 2.0 g of boron/potassium nitrate as a transfer charge. The inflator was set in a 60-liter tank and actuated by applying a current to ignition means to thereby ignite the pellet sample. Thereafter, there were determined the maximum pressure in the combustion chamber (MPa) and the time in which the internal pressure of the combustion chamber reaches the maximum (ms). After burning, the amount of effluent residue in the 60-liter tank was measured. The results are shown in Table 4.

TABLE 4

| | Example 5 | Com.Ex. 4 |
|---|---|---|
| Maximum pressure in combustion chamber (MPa) | 22.7 | 24.3 |
| Time for pressure in combustion chamber to reach maximum (ms) | 12.6 | 12.8 |
| Amount of effluent residue in 60 liter-tank (g) | 0.19 | 1.92 |

Table 4 shows that when the gas generating composition of the invention is used, the amount of the effluent residue in 60-liter tank after burning can be reduced to 1/10 or less.

TEST EXAMPLE 5

Forty-five grams of each of the pellet samples of the gas generating compositions prepared in Example 5 and Comparative Example 4 was individually filled into the combustion chamber of an inflator having a gas outlet 3 mm in diameter and loaded with 2.0 g of boron/potassium nitrate as a transfer charge. The inflator was set in an air bag module for a driver's seat, and then actuated to inflate the air bag. Thereafter the air bag was checked for damage.

When the pellets of the gas generating composition obtained in Example 5 were used, no damage was detected in the air bag. On the other hand, when the pellets of the gas generating composition obtained in Comparative Example 4 were used, the air bag has partly fused.

EFFECTS OF THE INVENTION

The manganese complex of the formula (1) according to the invention showed weight loss of only 1% or less even under the rigorous conditions of 400-hour heating at 107° C. The complex has significantly improved heat stability and is a compound usable as an active component of an air bag gas generating composition which can endure the use for a long term of at least 10 to 15 years.

That is to say, the manganese complex of the invention even after an accelerated heating test can satisfy the property requirements for conventional air bag gas generating compositions.

The air bag gas generating compositions A and B according to the invention are azide-free air bag gas generating compositions, are superior in heat resistance and can withstand the use for a long term of at least 10 to 15 years even under severe conditions.

Furthermore, the air bag gas generating composition B according to the invention features a high rate of combustion residue in an inflator.

We claim:

1. A manganese complex represented by the formula (1)

  (1)

and showing weight loss of not higher than 1% after heating at 107° C. for 400 hours.

2. The manganese complex according to claim 1 which has weight loss of not higher than 0.5% after heating at 107° C. for 400 hours.

3. The manganese complex according to claim 1 or 2 which can be prepared by reacting manganese nitrate with semicarbazide in an atmosphere of inert gas.

4. An air bag gas generating composition which comprises a manganese complex represented by the formula (1)

  (1)

and showing weight loss of not higher than 1% after heating at 107° C. for 400 hours, and an oxidizing agent.

5. The air bag gas generating composition according to claim 4 which comprises the manganese complex of the formula (1) showing weight loss of not higher than 0.5% after heating at 107° C. for 400 hours, and an oxidizing agent.

6. The air bag gas generating composition according to claim 4 or 5 which contains a manganese complex which can be prepared by reacting manganese nitrate with semicarbazide in an atmosphere of inert gas.

7. The air bag gas generating composition according to claim 4 or 5, wherein the oxidizing agent is a salt of nitric acid.

8. The air bag gas generating composition according to claim 7, wherein the salt of nitric acid is at lease one member selected from the group consisting of potassium nitrate and strontium nitrate.

9. The air bag gas generating composition according to claim 4 or 5 which contains 10 to 400 parts by weight of the oxidizing agent per 100 parts by weight of the manganese complex.

10. An air bag gas generating composition which comprises a complex mixture of (a) a manganese complex represented by the formula (1)

  (1)

and showing weight loss of not higher than 1% after heating at 107° C. for 400 hours and (b) a magnesium complex represented by the formula (2)

  (2)

wherein X is $H_2NNHCONH_2$ or $H_2NNHCONHNH_2$, the mixing ratio, in terms of a weight ratio, of the component (a) to the component (b) being 5:57-57:5, and an oxidizing agent.

11. The air bag gas generating composition according to claim 10, wherein the component (a) is a manganese complex showing weight loss of not higher than 0.5% after heating at 107° C. for 400 hours.

12. The air bag gas generating composition according to claim 10, wherein the component (b) is a magnesium complex of semicarbazide represented by the formula (3)

  (3).

13. The air bag gas generating composition according to claim 10, wherein the component (b) is a a magnesium complex of carbohydrazide represented by the formula (4)

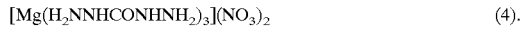  (4).

14. The air bag gas generating composition according to claim 10, 11, 12 or 13, wherein the mixing ratio, in terms of a weight ratio, of the component (a) to the component (b) is 20:42–52:10.

15. The air bag gas generating composition according to claim 10, 11, 12 or 13, wherein the mixing ratio, in terms of a weight ratio, of the component (a) to the component (b) is 35:27–45:17.

16. The air bag gas generating composition according to claim 10 or 11, wherein the oxidizing agent is a salt of nitric acid.

17. The air bag gas generating composition according to claim 16, wherein the salt of nitric acid is at least one member selected from the group consisting of potassium nitrate and strontium nitrate.

18. The air bag gas generating composition according to claim 10 or 11 which contains 10 to 400 parts by weight of the oxidizing agent per 100 parts by weight of the complex mixture.

* * * * *